United States Patent [19]

Sacristan

[11] Patent Number: 5,455,417
[45] Date of Patent: Oct. 3, 1995

[54] ION MOBILITY METHOD AND DEVICE FOR GAS ANALYSIS

[76] Inventor: Emilio Sacristan, 7 Harvard St., Apt. 6, Worcester, Mass. 01608

[21] Appl. No.: 238,614

[22] Filed: May 5, 1994

[51] Int. Cl.⁶ .................................................. H01J 49/40
[52] U.S. Cl. ........................................ 250/287; 250/282
[58] Field of Search ................................ 250/287, 282; 324/464

[56] References Cited

U.S. PATENT DOCUMENTS

| | | | |
|---|---|---|---|
| 3,668,382 | 6/1972 | Cohen et al. | 250/41.9 |
| 4,193,296 | 3/1980 | Janka | 73/194 |
| 4,368,388 | 1/1983 | Blyth | 250/283 |
| 4,423,739 | 1/1984 | Passaro et al. | 128/719 |
| 4,445,038 | 4/1984 | Spangler et al. | 250/287 |
| 4,480,190 | 10/1984 | Burough et al. | 250/343 |
| 4,596,931 | 6/1986 | Ehnholm et al. | 250/343 |
| 4,633,083 | 12/1986 | Knorr et al. | 250/282 |
| 4,704,536 | 11/1987 | Sugiyama et al. | 250/381 |
| 4,724,394 | 2/1988 | Langer et al. | 324/464 |
| 4,777,363 | 10/1988 | Eiceman et al. | 250/286 |
| 4,831,254 | 5/1989 | Jenkins | 250/287 |
| 4,953,407 | 9/1990 | Malaczynski et al. | 73/861.09 |
| 5,047,723 | 9/1991 | Puumalainen | 324/464 |
| 5,117,107 | 5/1992 | Guilhaus et al. | 250/287 |
| 5,184,015 | 2/1993 | Allman et al. | 250/282 |
| 5,189,301 | 2/1993 | Thekkadath | 250/287 |
| 5,200,614 | 4/1993 | Jenkins | 250/286 |
| 5,218,203 | 6/1993 | Eisele et al. | 250/288 |
| 5,234,838 | 8/1993 | Bacon, Jr. | 436/173 |
| 5,235,182 | 8/1993 | Avida et al. | 250/286 |

FOREIGN PATENT DOCUMENTS 2198579  6/1988  United Kingdom.

OTHER PUBLICATIONS

Tammet H. F., *The Aspiration Method for the Determination of Atmospheric–ion Spectra*, Scientific Notes of Tartu State University, Issue 195, Transactions on Air Ionization and Electroaerosols, Tartu Estonia, 1967, Translated from Russian Israel Program for Scientific Translations, Jerusalem 1970, Chapter I.

Eiceman G. A., et al., "Ion Mobility Spectrometry of Halothane Enflurane, and Isoflurane Anesthetics in Air and Respired Gases," *Anal. Chem.* 61:1093–1099, (1989).

Hill H., "Ion Mobility Spectrometry," *Analytical Chemistry*, 62(23):1201A–1209A, (1990, Dec.).

Eiceman G. A. "Advances in Ion Mobility Spectrometry," *Critical Reviews in Analytical Chemistry*, 22(1,2):17–36, (1991).

Primary Examiner—Jack I. Berman
Attorney, Agent, or Firm—Hamilton, Brook, Smith & Reynolds

[57] ABSTRACT

A technique for measuring analyte concentration and a modulated aspiration condenser capable of performing this technique. The method for detecting the analyte comprises first collecting and ionizing a gas sample including the analyte in which the concentration of the analyte is high enough to completely saturate ionization process. The ion mobilities of ions contained in the ionized gas sample are determined. On the basis of the mobilities, a concentration of the analyte in the gas sample is determined. The modulated ion mobility detector comprises an ionizer ionizing a continuously flowing gas sample. A detection cell receives the ionized gas sample in which a reference plate and a collection electrode establish a time varying electric field in a direction transverse to the direction of flow of the gas sample in the detection cell. Ions contained in the gas sample are thereby deflected into the collection electrode. A controller detects an electric current from the collection electrode and from this information determines mobilities of the ions. It should be noted, however, that the modulated aspiration condenser itself has wider application in measuring the mobility of any ion in virtually fluid and is not limited to anesthetic gas applications.

26 Claims, 8 Drawing Sheets

ION MOBILITY METHOD AND DEVICE FOR GAS ANALYSIS

BACKGROUND OF THE INVENTION

The elimination of pain, although of obvious importance, is not the primary role of an anesthesiologist. The anesthesiologist's foremost task involves maintaining an equilibrium of the functions of vital organs in the face of disequilibrating effects of disease, surgery, and pharmacologic interventions, including anesthesia. This balance is preserved through frequent measurements and adjustments of respired and blood gases, respiratory rate, blood pressure, heart rate, and other vital signs. Continuous and fast monitoring of inspired and expired anesthesia gases can significantly improve the efficacy of the procedure, satisfying the increasing demands of modern surgery and significantly improving the quality of care.

Another convincing argument for the continuous anesthesia monitoring is patient safety. In 1988, the nine hospitals affiliated with Harvard Medical School undertook a retrospective study of the last 12 years and found that some $5 million in projected insurance payouts could have been prevented in their own institutions, if patient monitoring had been routinely used. Furthermore, it found that the rate of accidents in anesthesia fell threefold when minimum monitoring standards for every anesthetic administered were made mandatory in 1985.

The three most commonly used anesthetic agents are volatile halogenated organic compounds: Halothane (Fluothane®, Wyeth-Ayerst Labs., Philadelphia, Pa.), Enflurane (Ethrane®, Ohmeda, Madison, Wis.), and Isoflurane (Forane®, Ohmeda, Madison, Wis.). Two new agents have recently been developed, Desflurane (Suprane®, Ohmeda, Madison, Wis.) and Sevoflurane (Abbott, Abbott Park, Ill.). In clinical anesthesia, the vapors of these agents are mixed into the breathing mixture with the use of calibrated vaporizers. Only one anesthetic agent is used at a time. The agent concentration in the breathing circuit mixture may range from 0 to 5% for Halothane, Sevoflurane, and Isoflurane, 0 to 7% for Enflurane, and 0–18% for Desflurane.

There are a few available technologies capable of measuring and identifying anesthetic gas. Mass spectrometry was the first methodology used clinically that provided accurate analysis of all of the gases and agents used in anesthesia. In another technology, Raman spectrometer, a powerful UV laser beam is reflected many times across the gas sample and Raman scattered light is detected at right angles to the laser beam. Infra-red spectroscopy analyzes multiple infra-red wave bands to identify specific anesthetic agents.

SUMMARY OF THE INVENTION

Each of the conventional technologies for measuring anesthetic gas concentration has the disadvantage of being expensive to implement. Further, the Raman spectrometer, for example, involves fragile components that require periodic maintenance.

The present invention concerns a more robust and inexpensive approach to measuring anesthetic gas concentration or for the matter many different organic and other chemicals in gas samples. Specifically, the invention concerns both a technique for measuring analyte concentration and a modulated aspiration condenser capable of performing this technique. It should be noted, however, that the modulated aspiration condenser itself has wider application in measuring the mobility of any ion in virtually any fluid and is not limited to anesthetic gas applications specifically described herein.

The inventive method for detecting anesthesia concentration comprises first collecting and ionizing a gas sample containing the analyte in which the concentration of the analyte is high enough to completely saturate ionization process. The ion mobilities of ions contained in the ionized gas sample are determined. On the basis of the mobilities, a concentration of the analyte in the gas sample is determined.

In a specific embodiment, the concentration of the analyte is determined in response to shifts in the ion mobilities in the ion mobility spectrum for complex ion clusters. The gas sample is generally collected from a patient's breathing circuit.

Considering the inventive ion mobility detector, it comprises an ionizer ionizing a continuously flowing gas sample. A detection cell receives the ionized gas sample in which a reference plate and a collection electrode establish a time varying electric field in a direction transverse to the direction of flow of the gas sample in the detection cell. Ions contained in the gas sample are thereby deflected into the collection electrode. A controller detects an electric current from the collection electrode and from this information determines mobilities of the ions.

In specific embodiments, the ion mobility detector further comprises a temperature controller controlling a temperature of the gas sample prior to entering the detection cell. Also, the controller controls the electric field to swept over a range of interest to generate a transformed ion mobility spectra in the form of a current to collector electrode/reference plate voltage characteristic.

According to another aspect, the present invention features a modulated aspiration condenser that comprises an ionizer ionizing received gas samples and a detection cell that receives the ionized gas samples. A reference plate and a collection electrode establish an electric field in the detection cell to deflect ions contained in the gas sample into the collection electrode. The collection plate has a characteristic capturing efficiency of the ions. A controller then modulates this capturing efficiency of the collection plate and detects an electric current from the collection electrode to determine mobilities and amounts of the ions.

In specific embodiments, the gas sample is a highly saturated concentration of an anesthetic agent and the controller determines a concentration of the anesthetic agent in the gas sample in response to ion mobilities of the ions.

According to another aspect, the invention features a method for detecting molecules in a gas sample. This method comprises first ionizing a gas sample and then detecting ions in the gas sample with an electric field established between a reference plate and a collection electrode. The collection electrode has a characteristic capturing efficiency of the ions. This capturing efficiency of the collection electrode is then modulated and the molecules identified in response to an electric current of the collection electrode for different capturing efficiencies of the collection electrode.

In specific embodiments, the capturing efficiency of the collection electrode is modulated by modulating the electric field.

The above and other features of the invention, including various novel techniques, steps, and details of construction and combinations of parts, and further advantages flowing from these configurations and processes, will now be more particularly described with reference to the accompanying drawings and pointed out in the claims. It will be understood that the particular technique for measuring anesthetic gas concentration and modulated aspiration condenser embodying the invention is shown by way of illustration and not as a limitation of the invention since the principles and features of this invention may be employed and varied in numerous embodiments without departing from its true scope.

DETAILED DESCRIPTION OF THE INVENTION

Figure 1:
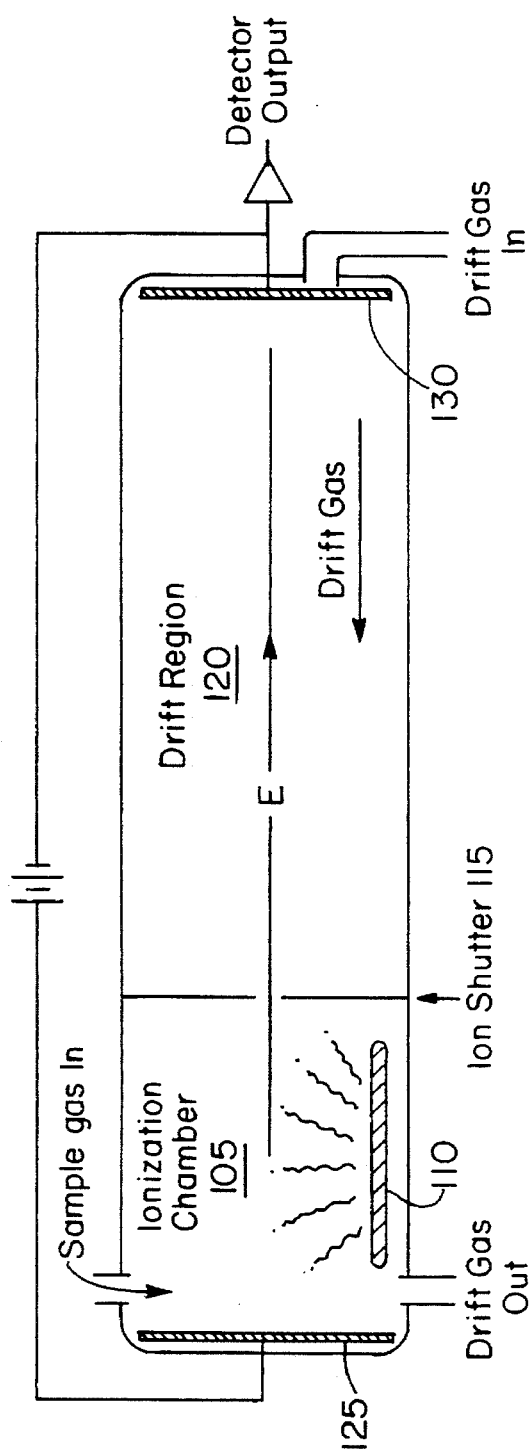
FIG. 1 schematically shows a prior art ion mobility drift tube.

Ion mobility spectrometry (IMS), or plasma chromatography as it was originally called, was introduced in the late 1960's as a method of detecting trace concentrations of organic compounds in air and other gases. In an ion mobility drift tube shown in FIG. 1, sometimes called time-of-flight analyzer, sampled gas is ionized in a reaction or ionization chamber 105 by an ionizing source 110. Typically, the ionization is produced with β-radiation.

Figure 2:
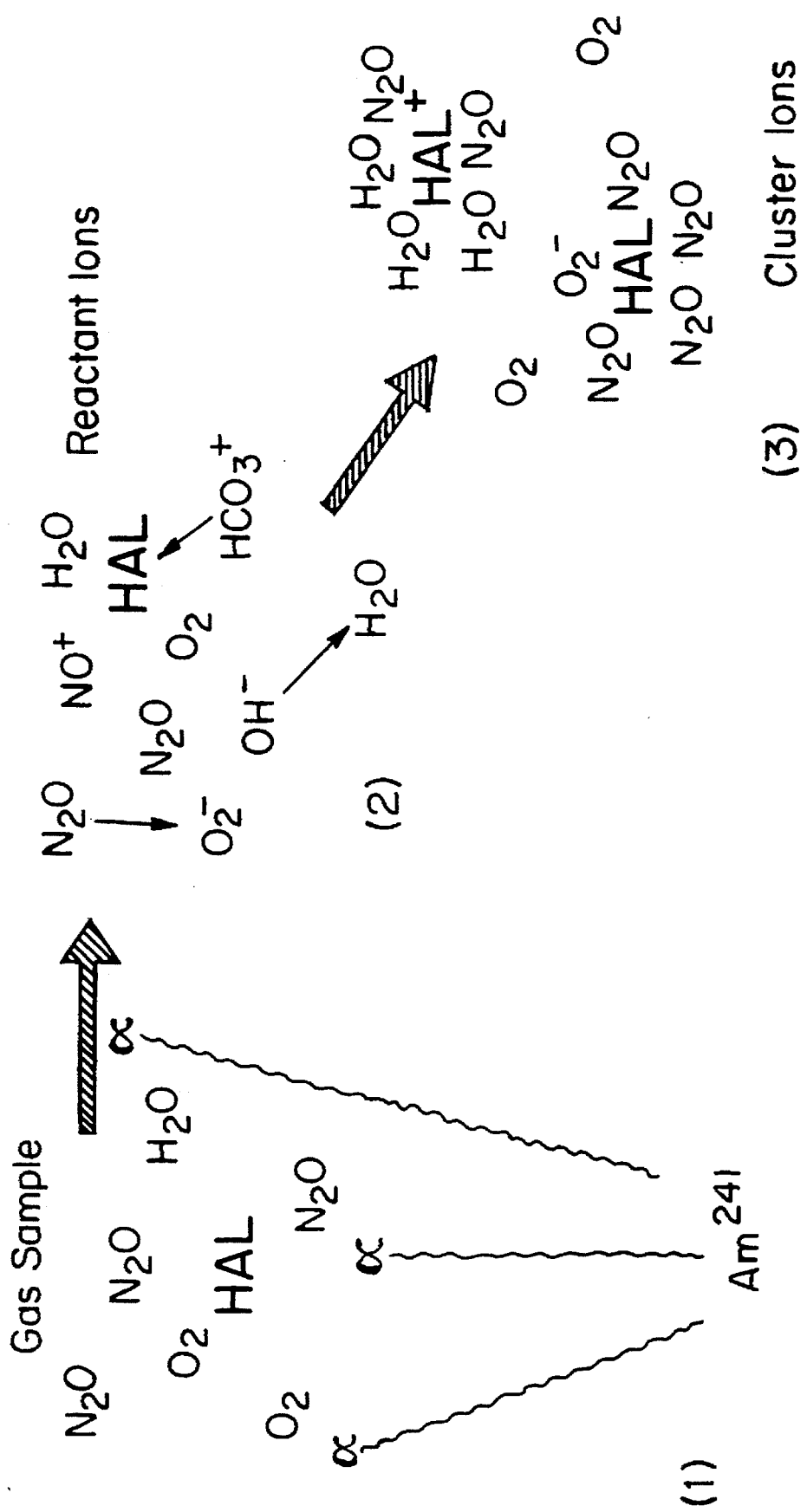
FIG. 2 illustrates the formation of ion clusters in sampled gas after ionization.

The most abundant ions formed in air by the ionizing radiation, called the reactant ions, are $H^+$, $NO^+$, $OH^-$, and $O_2-$, which are formed from gas molecules as shown in FIG. 2. Trace concentrations of an analyte HAL, such as an halogenated anesthetic agent, react with these ions and free electrons to form product ions of the analyte molecule, HAL, such as $HAL^+$, $HALH^+$, $HAL^-$ and $HAL*O_2-$. Polar molecules, $N_2O$ and $H_2O$ in particular, are attracted to these ions thereby forming ion clusters such as $(H_2O)_n(N_2O)_m*HAL-$.

Returning to FIG. 1, an ion shutter 115 is then opened to allow the ionized gas sample to enter the drift region 120. An electric field is established between a reference plate 125 and collection electrode 130, at the end of the drift region 120. In the specific example shown, the electric field goes in the direction of the collection electrode 130 from the reference plate 125 so that the positively charged ions of the gas sample are drawn across the drift region 120.

Once in the drift region, ions move at a particular drift velocity that is a function of the electric field present in the drift region, the density of the drift gas, and the ions' size and charge. Drift gas flows in the opposite direction of the ions to keep the drift tube clean. The ions' mobility, however, is not substantially affected by this flow. The collector plate 130 at the distal end of the drift region 120 captures the ions as they arrive. The spectrum generated is a plot of the collector plate current versus the drift time, which is the time it takes for a specific ion to traverse the length of the drift region 120.

Ion mobility spectrometry provides a direct method for the experimental determination of the ion mobility distribution of an ionized gas sample. This distribution will be characteristic of the composition of the gas sample. Reactant ions are separated from product ions by their ion mobility. For standard applications of ion mobility spectrometry, substances are detected by the existence of a particular ion species at a given ion mobility, and the concentration of the substance can be related to the current for that particular mobility. This, however, is only possible if the concentration of the analyte does not saturate the ionization source, and the carrier gas remains constant, since the product ion species are determined by both the analyte and the carrier gas.

When the concentration of analyte organic molecules increases, the density of reactant ions decreases, and that of product ions increases, as more reactant ions lose their charge to form product ions. Ionization source saturation is reached when all of the reactant ions form product ions. At that point, further increases in analyte concentration cannot contribute to further increases in product ion density. The number of product ions is thus limited by the number of ions formed by the ionization process. For this reason, practical applications of this technology have been limited to the measurement of trace concentrations on the order of parts-per-million or parts-per-billion of organic substances in air or pure gases.

The use of a time-of-flight analyzer was evaluated for the detection of Halothane, Enflurane, and Isoflurane in air by Eiceman, et al. in *Ion Mobility Spectrometry of Halothane, Enflurane, and Isoflurane Anesthetics in Air and Respired Gases*, Anal. Chem. 61:1093–1099 (1989). In that study, an ion mobility spectrometer with a $Ni^{63}$ ionization β-source was used, in conjunction with a mass spectrometer, to analyze and identify the product ions formed from the three volatile anesthetic agents at concentrations from 10 to 500 ppb. Easily identifiable negative molecular product ions, with distinct ionic mobilities, were found to be formed but within a very limited linear range. Measurements were made at 40° and 150°, in air; the effects of $N_2O$ and other variations in the composition of the carrier gas were not characterized. The authors of this study conceded that standard electronic and physical configurations of ion mobility spectrometers are not well suited for dosimetry measurements of the halogenated anesthetics since the concentration involved, 0.5–15%, far exceeded the saturation threshold. It has been suggested that in order to make standard IMS measurements of the anesthetic agents as described above, in a surgical patients breathing circuit where agent concentrations are above the saturation limits of the IMS by a factor of $10^4$, the sampled gas would have to be diluted in air under precise control.

Experimentation using a time-of-flight analyzer has revealed that with a gas sample containing a high concentration of a halogenated anesthetic so that the ionization process is completely saturated, the peak shape of the ion mobility is essentially static, yet the peak ion mobility shifts as a function of concentration. As the concentration of anesthetic is increased in an unsaturated gas sample, the various peaks associated with different ion species cease growing, and then as saturation occurs, the peaks begin to spread out becoming less pronounced. This spreading continues until a certain threshold concentration is reached after which a single, well defined, peak appears. Because the product ions have reached saturation, further increases in concentration does not affect the amplitude of this ion peak from the highly saturated gas sample. Under these conditions the standard IMS measurements of the amplitude of selected ion mobility peaks are not correlated to analyte concentration. Ion mobility indicated by this peak, however, changes as a function of the concentration.

Figure 3:
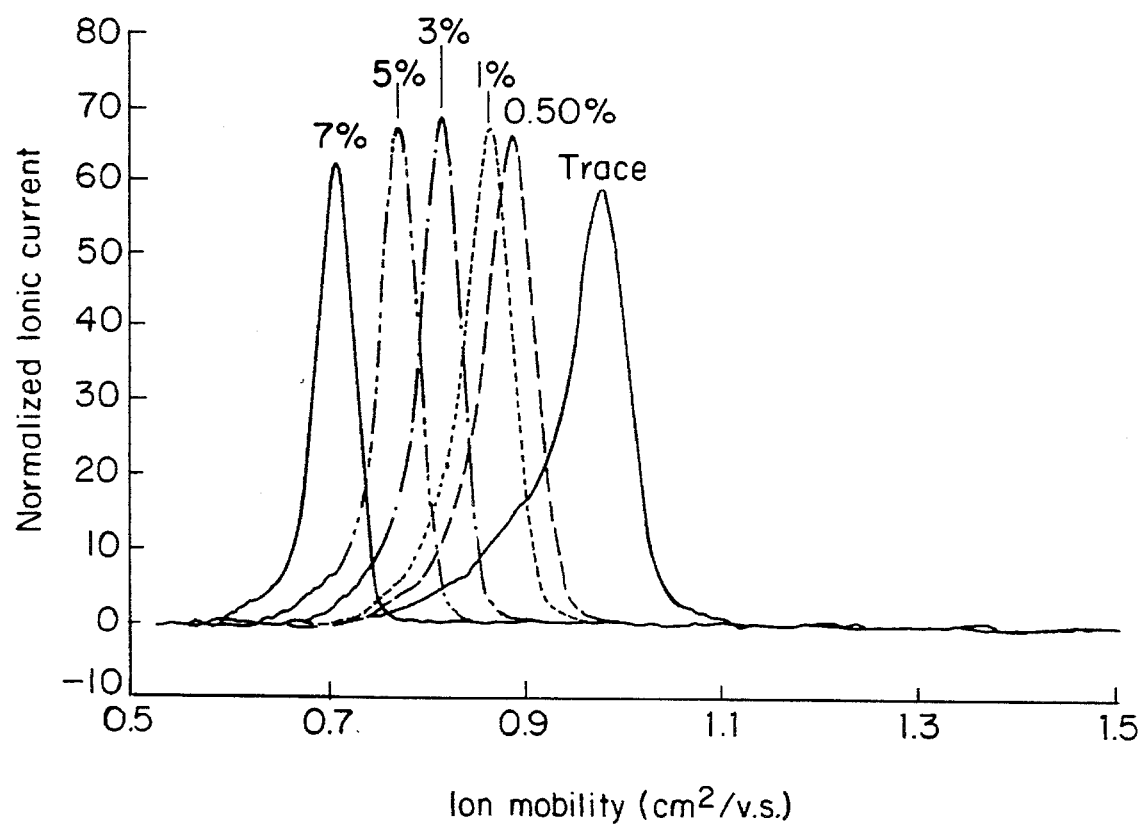
FIG. 3 shows the ion mobility spectra for various concentrations of Enflurane under saturated ionization.

FIG. 3 is a plot of normalized ionic current for negative ions versus ion mobility for varying concentrations of Enflurane in 40% $O_2$/50%$N_2$O/bal. $CO_2$ @40% RH. The peak shapes for the various concentrations, trace, 0.50%, 1%, 3%, 5%, and 7% remain relatively constant and well defined. The peak positions, however, shift in an experimentally reproducible manner as a function of the Enflurane concentration.

The determination of anesthetic agent concentration is most accurately made by measuring the current of negative ions since the peak ion mobility of these ions is most sensitive to changes in agent concentration. Furthermore, negative ion spectra are most sensitive in the low concentration range, where more accuracy is required. In addition, negative ions are insensitive to variations in humidity of the sample.

From the results of IMS studies of highly saturated gas samples, it is readily apparent that large ion clusters are being formed from these anesthetic gas mixtures. The ion mobility of the product ions is between 0.5 and 1.2 $cm^2$/Vs as opposed to the product ions of trace concentrations of anesthetic agents in air measured by Eiceman, supra, where ion mobilities ranged from 1.3 to 1.7 $cm^2$/Vs. The continuous shift of the highly saturated ion mobility peak, instead of the growth of new peaks, is probably due to the existence of at least two ion cluster species, and to single ion clusters changing size during flight. The change in ion mobility is due to a change in average ion cluster size.

Figure 4:
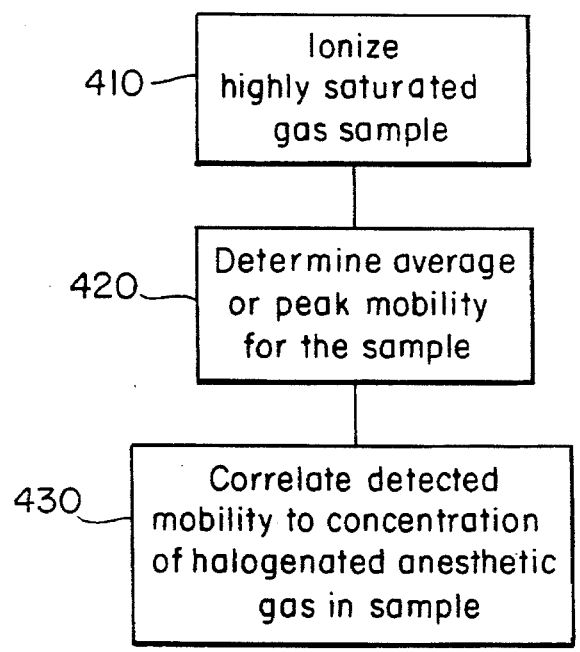
FIG. 4 illustrates a method of the invention for determining halogenated anesthetic gas concentrations in highly saturated samples.

FIG. 4 shows a method for determining concentration of vaporized organic compounds such as halogenated anesthetic gas in saturated samples. Specifically, in step 410 a gas sample having an unknown concentration of a known halogenated anesthetic gas is ionized. The concentration of anesthetic agent is high enough to saturate the ionization process. That is, when the sample is ionized, the number of anesthetic gas molecules, or analyte ions generally, will exceed the number of reactant ions that are formed from the gas molecules. Then, in step 420 a peak or average ion mobility of the negative ions is calculated using, for example, time-of-flight analyzer or the modulated aspiration condenser described below. Since large cluster of ions will form, the detected mobility will be for these clusters. The detected peak or average mobility is then correlated to mobilities in this type of gas sample for known concentrations in step 430. On the basis of this correlation, an estimation of the concentration of the organic agent is generated. Large changes in $N_2O$ and $CO_2$ in the carrier gas cause significant variations in ion measurements and will require control. Temperature is also a critical factor, and should be actively stabilized.

The inventive method will work for ionizable polar chemical gas, vapor, or aerosol that in high enough concentrations will form large complex ion clusters with an ion mobility that is directly related to analyte concentration. In addition, this method can be used to measure the gases in the carrier gas itself, as opposed to standard ion mobility spectroscopy. Variations in the carrier gas mixture affect not only the formation of the ion clusters but also the density of the drift gas, therefore changing the mobility of the reactant ions as a function of gas composition. This method has been used successfully to estimate the concentration of O2, CO2, and N20 in mixtures of air and anesthesia gas. For chemicals that don't form stable long-lived ions, an organic dopant can be added to the sample in a controlled and constant concentration so that the analyte can form clusters around the dopant ions, and the inventive method can then be used to relate ion mobility measured to the concentration of the analyte. Applications of this method include for example, but not limited to, the analysis of war gases, explosives, drugs and pharmaceutical, exhaust gases, metabolic by-products, industrial by-products, etc. Another specific application related to anesthesia monitoring is measuring the cardiac output by inserting an inert gas such as a halocarbon into the breathing circuit and then measuring the clearance of the gas in the expired breath. For all of the above, the measurement device would have to be configured and calibrated for a specific application using the inventive method. The most important limitation of this methodology is that it cannot be used to analyze and identify unknown components of gas sample, unlike standard ion mobility spectroscopy methods.

As described above, time-of-flight analyzers provide adequate insight into ion mobility in gas samples highly saturated with halogenated anesthetic gas or other chemicals. Time-of-flight analyzers, however, have a number of drawbacks. First, they are not true in-line monitors since outside drift gas is introduced. Further, they do not provide a continuous measurement of concentration since the ion shutter must be used to release the ionized sample into the drift region. Still additionally, they require the added components such as the ion shutter and high voltages between the reference plate and the collection electrode.

In a technology related to time-of-flight analyzers, the anesthetic multigas analyzer is a hybrid ion mobility spectrometer based on the work of Puumalainen, U.S. Pat. No. 5,047,723, among others. Different ion mobilities are separated in space and measured simultaneously using multiple detectors instead of using a single detector and measuring different drift times. This system, illustrated in FIG. 5, has been called an aspiration condenser. Sampled gas is continuously fed into the device by a pump (not shown). The entering sampled gas is ionized by radiation from a radioactive source 520 and heated to a constant temperature in the ionization chamber 510. Ions formed are then carried by the gas flow through a detection cell 530. A deflecting electric field 540, on the order of 2 V/cm, is produced by a voltage difference between reference plates 550 and detector plates 560 on opposite walls of the cell 530. Neutral, or non-ionized, particles are unaffected by the electric field 540. Charged particles, however, are deflected by the electric field and eventually will hit the detection plates 560. The ions hitting the plates provide a current proportional to the charge and abundance of the ions. After the ions have hit the electrode, they disintegrate and all the molecules involved return to the flow stream in their neutral state.

Figure 5:
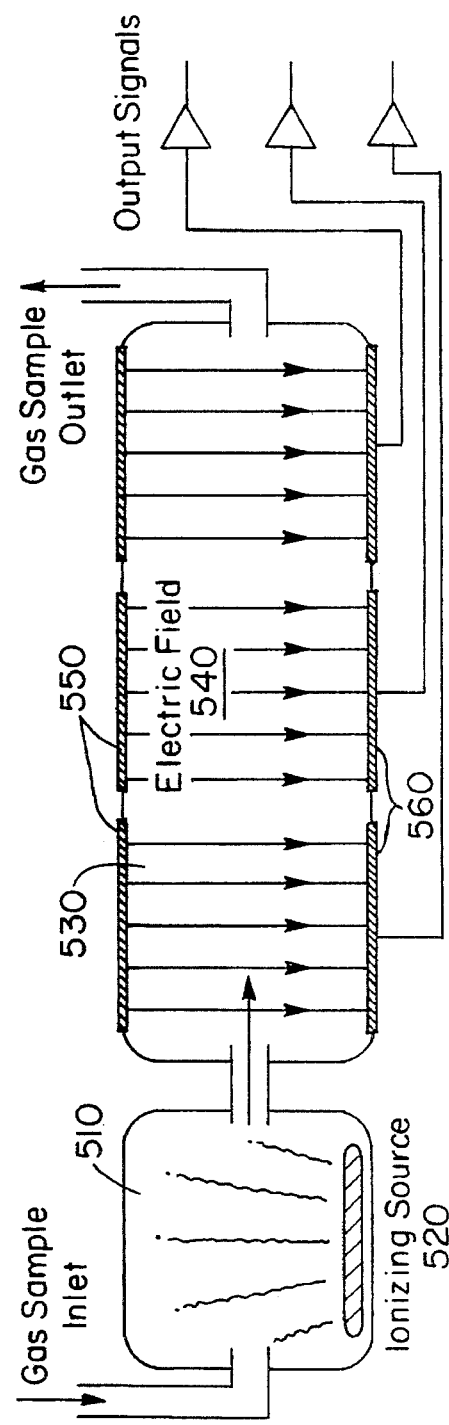
FIG. 5 is a schematic diagram of a prior art aspiration condenser.

A first order differential aspiration condenser is a simplified version of the device shown in FIG. 5. The first order condenser has certain advantages in detecting average ion mobility in highly saturated gas samples of halogenated anesthetics. This is because the capturing efficiency as a function of ion mobility, or G-function, has a linear range where ion current is proportional to ion mobility when peak shape remains substantially constant.

Figure 6:
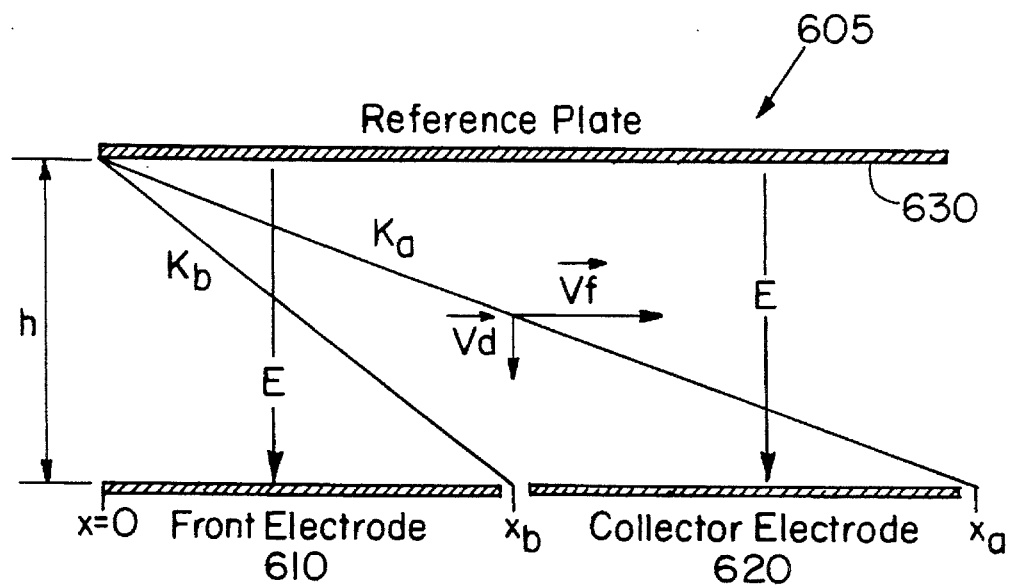
FIG. 6 is a schematic diagram of a detection cell of a prior art first order differential aspiration condenser.

The detection cell 605 of a first order differential condenser is shown schematically in FIG. 6. This type has only two independent electrodes, a front electrode 610 and a collection electrode 620 opposite a single reference plate 630. The sampled gas entering the detection cell 605 will have a x-axis velocity $V_f$ of the drift gas. Due to the direction of the electric field, as positive ions pass between the reference plate 630 and the electrodes 610, 620, the electric field E imparts a y-axis velocity $V_d$ to the ions which is a function of their mobility. To measure negative ions, the polarity of the field is simply reversed.

All positive ions having mobilities of $K_b$ or greater will be deflected sufficiently to be captured by the front electrode 610. This is because even ions entering the cell distance h from the electrodes, the far side of the detection cell, will be captured. From a similar analysis, all ions having a mobility of $K_a$ or greater will be captured by either the front electrode 610 or the collection electrode 620.

Figure 7:
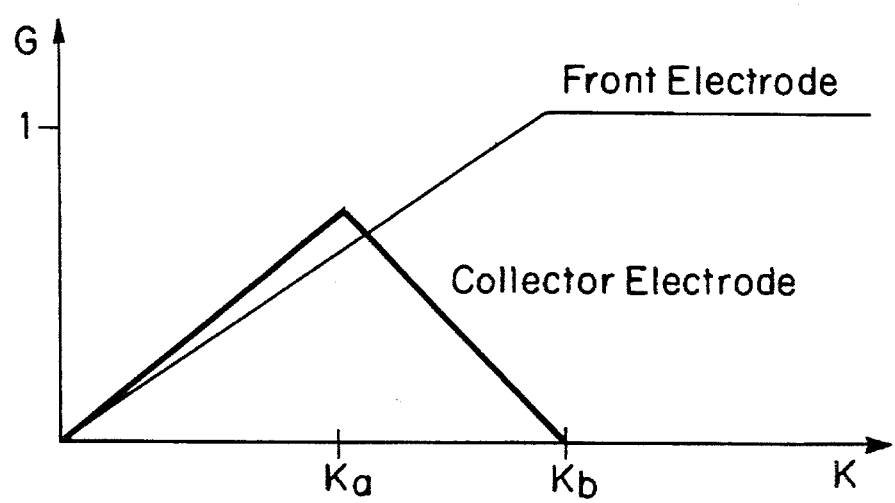
FIG. 7 shows exemplary capturing efficiencies as a function ion mobility, G-functions, of a front and collection electrode.

FIG. 7 illustrates the G-functions for both the front electrode 610 and the collection electrode 620. Their respective shapes can be understood intuitively by recognizing that for mobilities between 0 and $K_b$, the front electrode will progressively catch more ions as the ions' mobility increases until 100% efficiency is reached at a mobility of $K_b$. The front electrode 610 will catch some ion with very low mobilities because some of these ions will enter the chamber close to the front electrode requiring only small movement along the y-axis before being captured.

The G-function of the collection electrode 620 has a triangular shape rather than the ramp shape associated with the front electrode. This difference results from the fact that the sums of both of the G-functions for mobilities between $K_a$ and $K_b$ is 100% and less than 100% for mobilities between 0 and $K_a$.

Applying the information discussed previously concerning the relationship between ion mobility and concentration in highly saturated samples, the first order differential aspiration condenser can be used to detect anesthesia gas concentration. A collection electrode having a G-function as that illustrated in FIG. 7 will have a collection electrode current that is linearly related to ion mobility when the mobilities fall into the range of $K_a$ to $K_b$.

Figure 8:
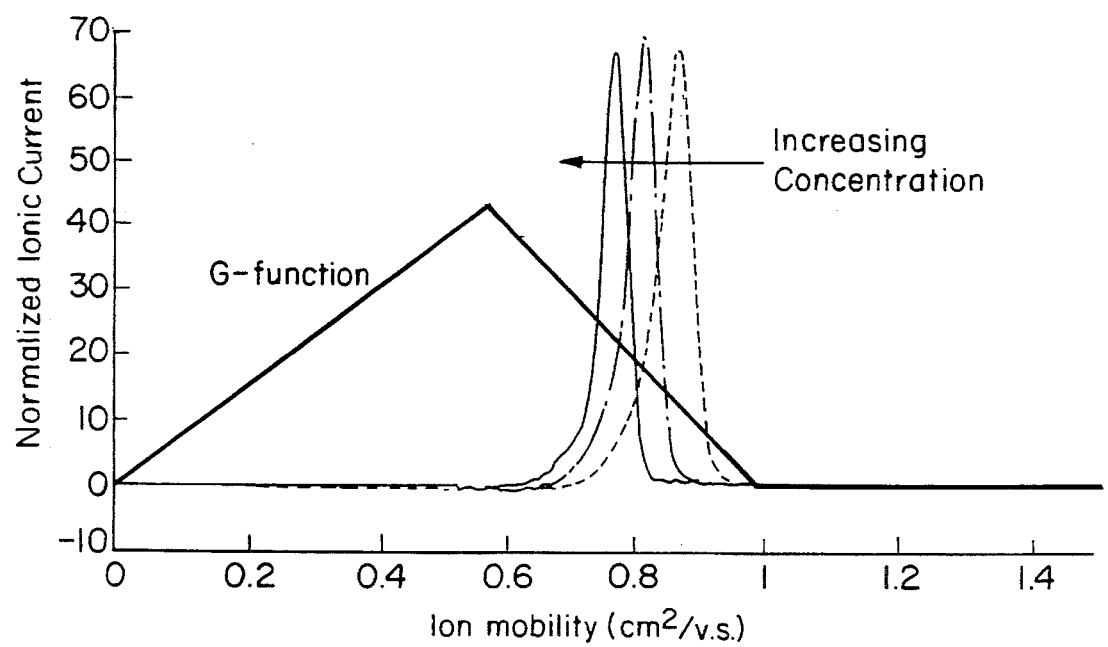
FIG. 8 is a graph of ionic current versus ion mobility for a collection electrode and the G-function for that electrode.

FIG. 8 illustrates a specific example of a G-function for a collector plate compared against an increasing ion mobility distribution. The specific collection electrode has a linear range between approximately $0.6 < K < 1$ cm$^2$/Vs. As ion mobility distribution changes characteristic of an increasing average peak ion mobility shift, the ion mobility curve remains essentially static but shifted. The collector electrode current is related to the integral of the G-function and the ion mobility distribution. Thus, the electrode current will be inversely proportional to peak mobility between 0.6 and 1 cm$^2$/Vs.

Figure 9:
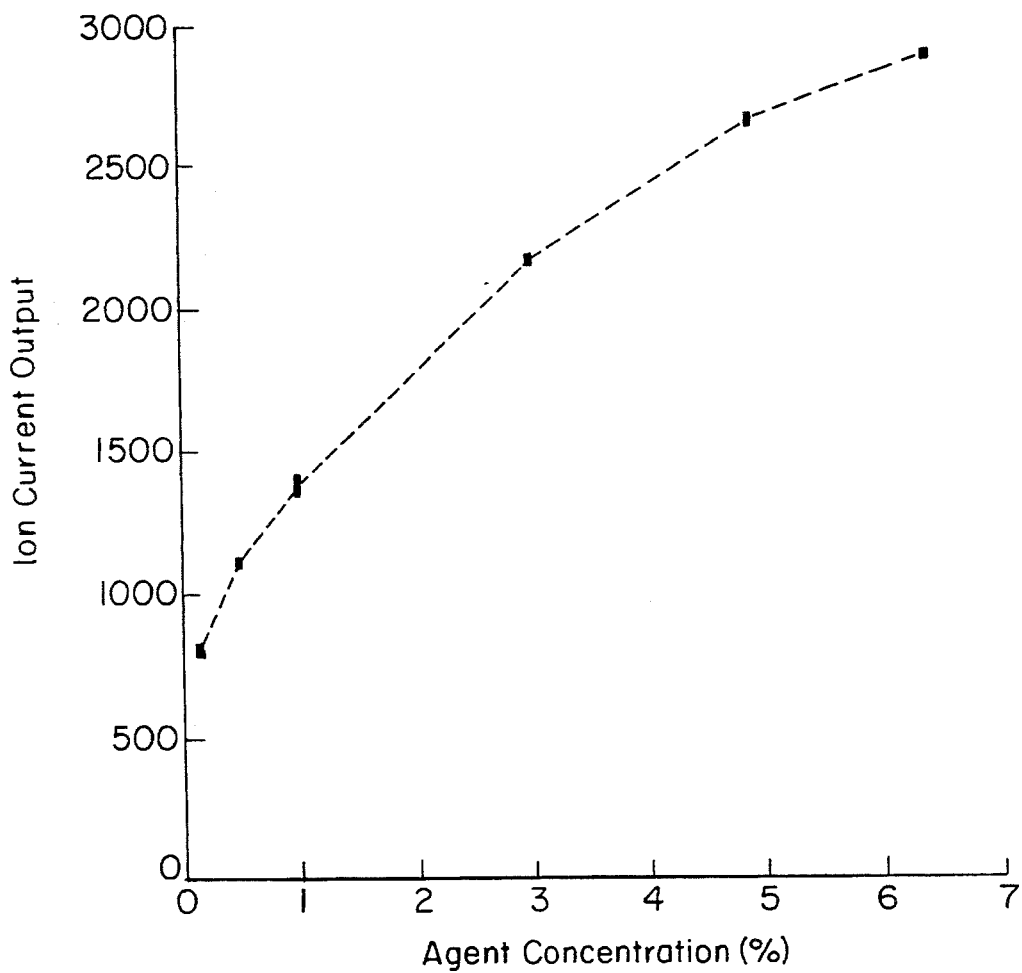
FIG. 9 is a calibration curve which relates ionic current to agent concentration for an aspiration condenser.

FIG. 9 shows plot of collector electrode current versus agent concentration, a calibration curve, for Enflurane in 50% $O_2$/50% $N_2O$ (each unit of the ion current axis corresponds to 16.7 $(10)^{-6}$ pA). Agent concentration is directly related to ion current output for a specific aspiration condenser operating at a set voltage and drift gas velocity. This plot shows how the relationship is nonlinear yielding greater sensitivity at lower ranges of concentration.

Conventional differential aspiration condensers have a number of drawbacks. The most important is the limited resolution of the measurement. Such a device is well suited to use the inventive method described above to measure analyte concentration, but there is more information contained in the shape of the ion mobility distribution of the sample that cannot be extracted with the averaging measurements of the conventional aspiration condenser. The shape of the ion mobility distribution may contain information on the specific anesthetic agent, or on the concentration of other components or possible interferents in the gas sample. In addition, variables such as temperature and flowrate affect ion mobility measurements and must be actively controlled.

Figure 10:
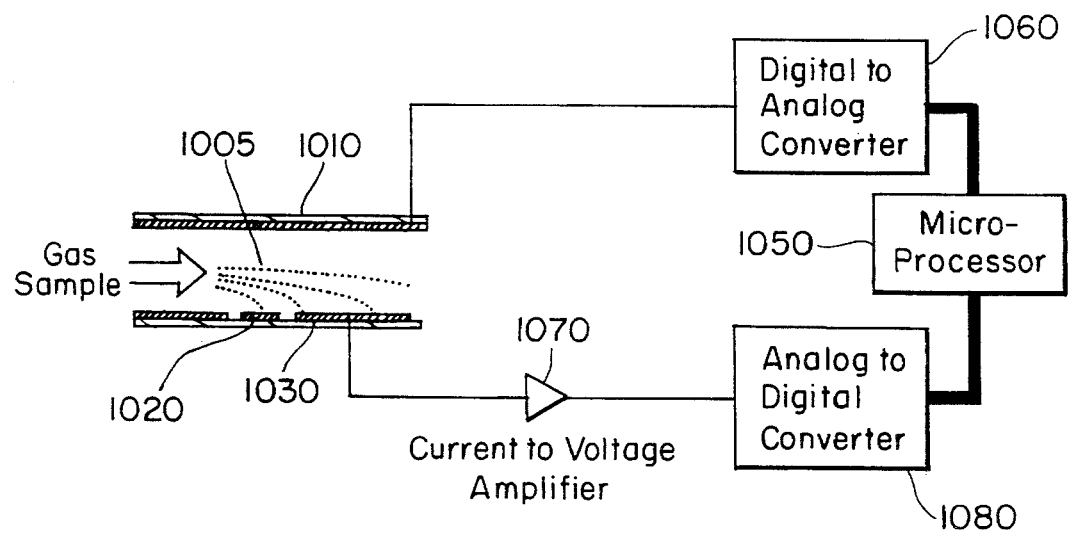
FIG. 10 is a schematic diagram of the inventive modulated aspiration condenser.

A more complete gas analysis can be generated by the inventive modulated aspiration condenser shown schematically in FIG. 10. This condenser is similar to conventional first order condensers in electrode layout in the detection cell except that the capturing efficiency or G-function of the collector electrode is modulated to apply a range of different functions to analyze the ion mobilities in the sampled gas. The G-function can be affected by modulating any one of a number of factors such aspiration condenser dimension, e.g. width, length, and electrode positions, drift gas velocity, drift gas temperature, and drift gas pressure. The preferred approach, however, is to modulate the electric field established in the detection cell 1005 between the reference plate 1010 and the front 1020 and collection electrodes 1030 using a microprocessor 1050. Specifically, the microprocessor 1050 generates digital data indicative of an desired instantaneous voltage of reference plate 1010. This digital data is then converted to an analog voltage by the digital to analog converter 1060. The ionic current generated by this instantaneous voltage is amplified by a current to voltage amplifier 1070 and converted to corresponding digital data by an analog to digital converter 1080, which is received by the microprocessor 1050.

Figure 11:
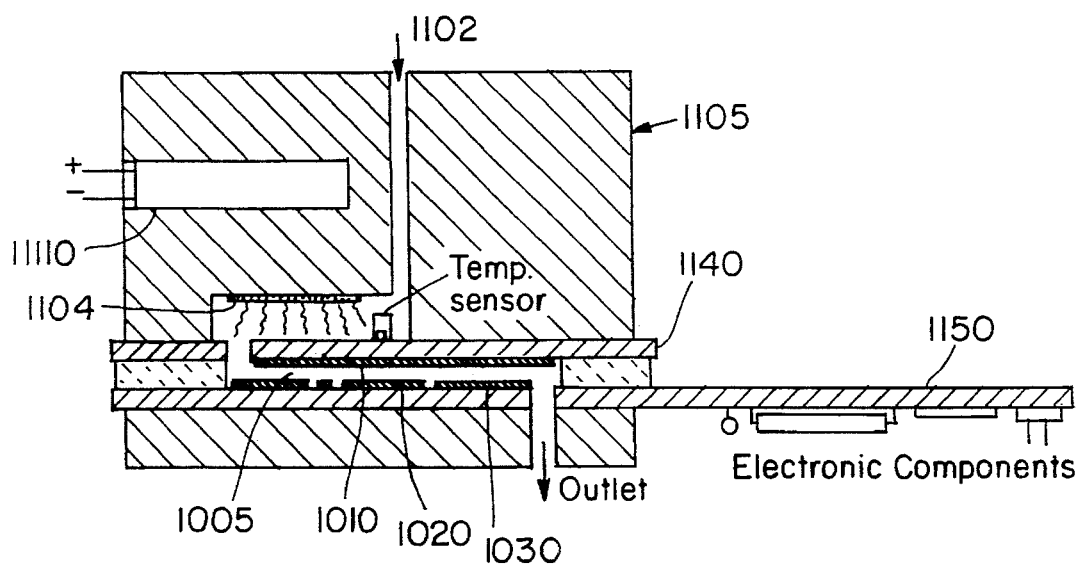
FIG. 11 is a cross-sectional view of the inventive condenser.

FIG. 11 shows a cross-sectional view of specific embodiment of the inventive condenser in which the same reference numerals as used in FIG. 10 indicate the same components. Incoming drift gas received through inlet 1102 is heated to a constant temperature by the aluminum block 1105 whose temperature is controlled by the heater 1110. The drift gas is then ionized by radiation from an Americium 241 sample 1104, Different ionizing sources could be used, however. For example, alpha or Beta radiation and photons are options from corona spray, laser, or radioactive sources. The ionized drift gas then enters the detection cell 1005. The detection cell 1005 has a reference plate 1010 spaced apart from series front and collection electrodes 1020, 1030. The distance between the references plate 1010 and the electrodes 1020, 1030 is approximately 0.5 mm. The detection cell 1005 has a length of approximately 3 cm. Also, the electrodes 1020, 1030, reference plate 1010, and associated circuitry 1050, 1060, 1070, and 1080 (not shown) are carried on printed circuit boards 1140, 1150.

For the aspiration condenser described in connection with FIGS. 10 and 11, a more complete analysis of the drift gas can be obtained. The preferred technique for modulating the voltage between the reference plate and collector electrode/front electrode is to change the voltage incrementally between −10 and 10 volts in 64 or 8 steps. After each voltage change, a delay of 10 ms is provided before the new voltage increment to allow the collector electrode current to stabilize for the new voltage.

Figure 12:
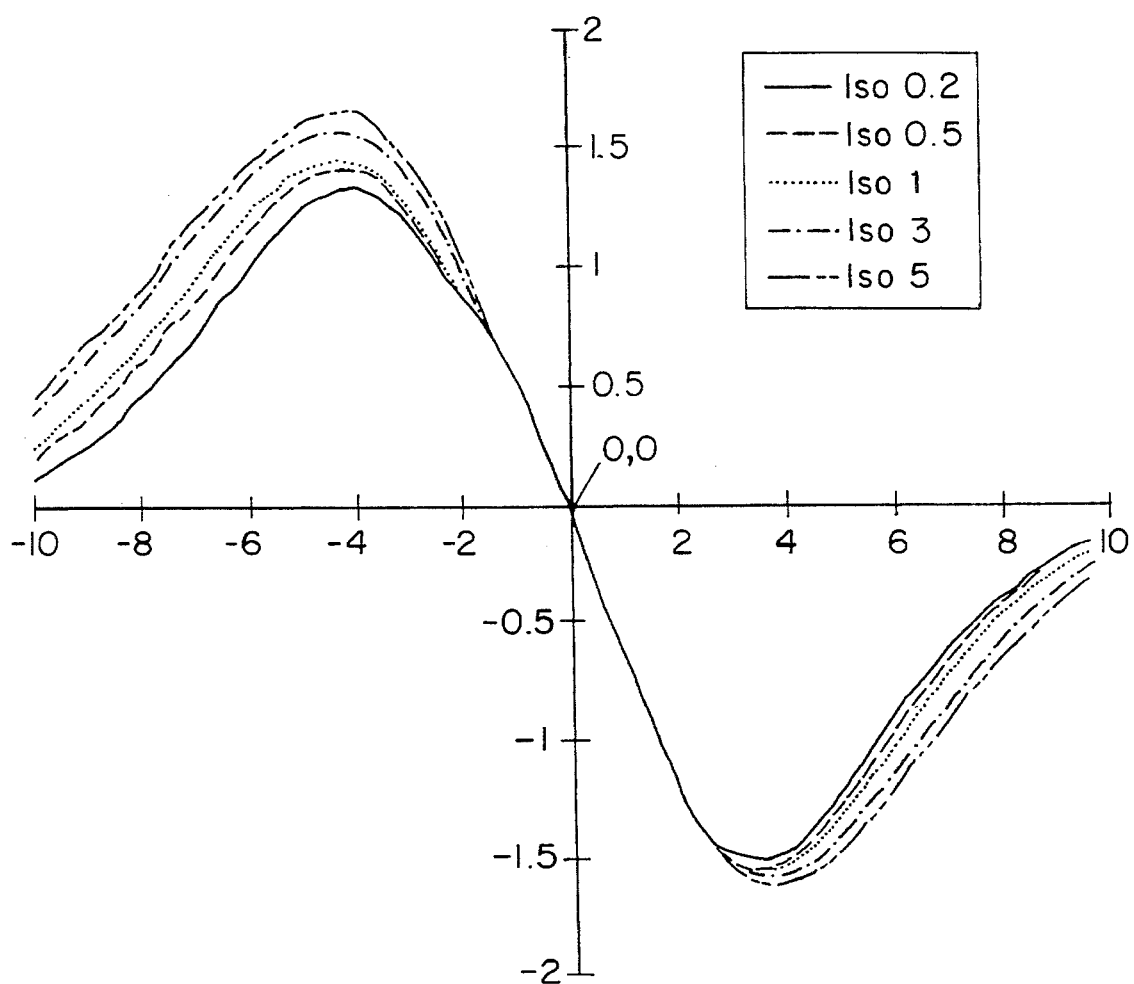
FIG. 12 are V-I curves for various concentrations of Isoflurane generated using the inventive condenser.

The incremental modulation of the collector voltage yields a V-I curve which is a result essentially of the application of 64 G-functions, or different plate characteristics, in analyzing the drift gas. V-I curves for different concentrations of Isoflurane are shown in FIG. 12. As illustrated by this figure, different concentration of Isoflurane have characteristically different V-I curves. By mathematical transformation, the V-I curves can be converted into ion mobility distributions as would be directly generated by a time-of-flight analyzer. Using a conventional unmodulated aspiration condenser only a single point on this V-I curve would be available to base an assumption on the Isoflurane concentration.

Figure 13:
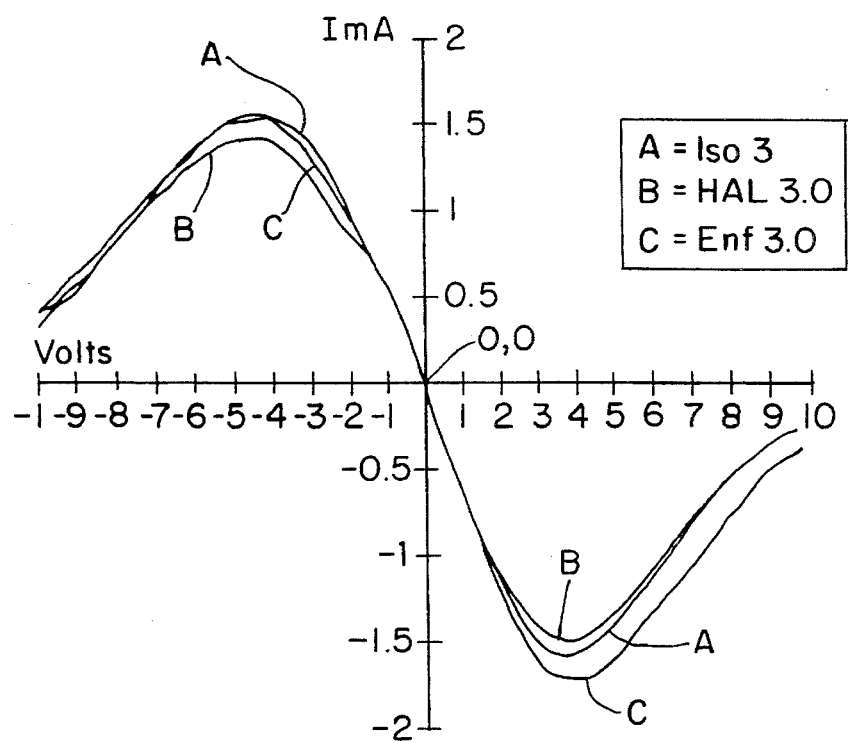
FIG. 13 are V-I curves for each of Isoflurane, Halothane, and Enflurane generated using the inventive condenser.

The V-I curve developed by the inventive aspiration condenser can also be used to identify different types of agents. FIG. 13 shows three different curves A, B, and C for each of Isoflurane, Halothane, and Enflurane, respectively. The aspiration condenser can be used as an agent identifier by comparing the shapes of these curves to expected ideal curves for each of the possible agents.

Figure 14:
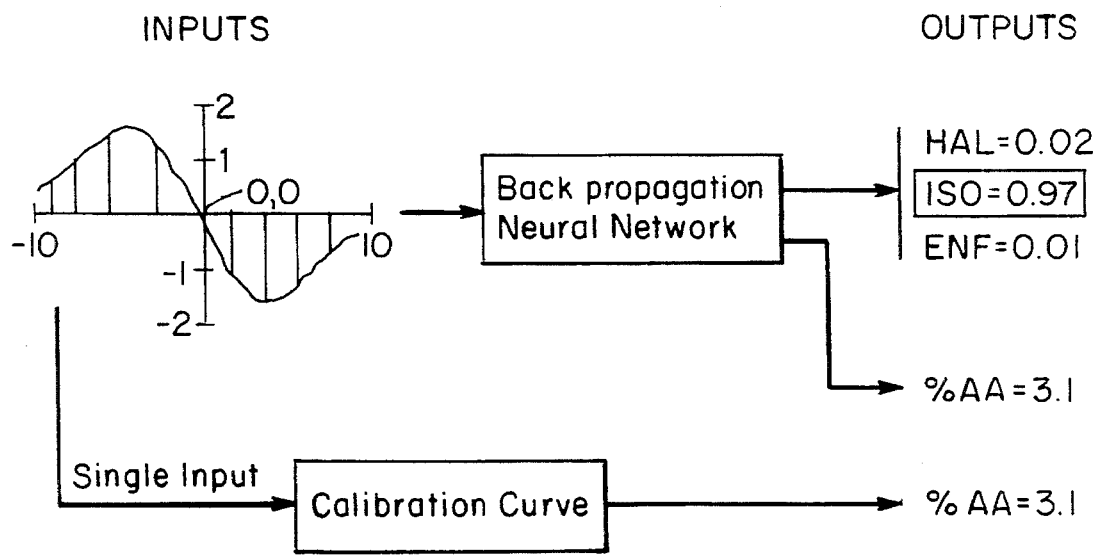
FIG. 14 illustrates a signal processing technique for identifying the type of anesthetic agent and its concentration.

Both agent identification and concentration of known agent relies on pattern matching. Obtaining a best fit to a variety of expected V-I curves is best done with a back propagation neural network as shown in FIG. 14. Here, the neural network generates a probability of a match between the experimental V-I curve and an ideal curves for each potential agent. Then, from the V-I data a determination of concentration is made based upon the predicted agent. The determination of neural network is then cross-checked against a calibration curve conclusion by only looking at a single collector plate current for a reference plate voltage which yields optimum G-function for the expected agent concentration. This cross-check provides a further level of redundancy.

The pattern recognition approach as well as other multivariate analysis techniques can also be used to determine the concentration of all components of an anesthesia gas mixture, given that all the components are known and the shape of the V-I curve is unique for each possible mixture. This means that in addition to measuring and identifying the anesthesia agent, the relative concentrations of $O_2$, $N_2O$, $CO_2$, and $N_2$, can also be estimated.

It should be emphasized again that although the inventive modulated aspiration condenser has been described in the specific application of monitoring halogenated anesthetic agent in expired gases, the inventive detector could be used to determine ion mobility in virtually any compatible fluid and for saturated or unsaturated samples.

In addition to the analysis method described in detail above, a great variety of pattern recognition, and multivariate statistical techniques exist and can be used to analyze the V-I curves obtained using the innovative modulated aspiration condenser.

Those skilled in the art will know or be able to ascertain using no more than routine experimentation, many equivalents to the specific embodiments of the invention described herein. These and all other equivalents are intended to be encompassed by the following claims.

I claim:
1. A method for detecting analyte concentration in a gas sample, comprising:
   collecting the gas sample containing the analyte;
   ionizing the gas sample, the concentration of the analyte being high enough to completely saturate an ionization process;
   determining ion mobilities of ions contained in the ionized gas sample; and
   determining a concentration of the analyte in the gas sample in response to the ion mobilities of the ions.

2. A method as claimed in claim 1, further comprising determining the concentration of the analyte in response to shifts in ion mobilities in an ion mobility spectrum of complex ion clusters.

3. A method as claimed in claim 1, further comprising determining the ion mobilities using an aspiration condenser.

4. A method as claimed in claim 1, further comprising collecting the gas sample from air in a breathing circuit of a patient.

5. A method as claimed in claim 1, wherein the gas sample includes a dopant in a fixed concentration to enable formation of stable ion clusters which include the analyte.

6. A method as claimed in claim 1, wherein the analyte is an anesthetic agent.

7. An ion mobility detector, comprising:
   an ionizer ionizing a flowing gas sample;
   a detection cell receiving the ionized gas sample;
   a reference plate and a collection electrode establishing a time varying electric field in the detection cell to deflect ions contained in the gas sample into the collection electrode; and
   a controller detecting an electric current from the collection electrode, and determining mobilities of the ions in response to the electric current of the collection electrode and magnitudes of the time varying electric field.

8. An ion mobility detector as claimed in claim 7, further comprising a heater controlling a temperature of the gas sample prior to entering the detection cell.

9. An ion mobility detector as claimed in claim 7, wherein the controller sweeps the electric field over a range of interest to generate a plot of the electric current of the collection electrode in response to instantaneous values of the time varying electric field.

10. An ion mobility detector as claimed in claim 7, wherein the time varying electric field is in a direction transverse to the direction of flow of the gas sample in the detection cell.

11. An ion mobility detector as claimed in claim 7, wherein the gas sample has a highly saturated concentration of an anesthetic agent.

12. An ion mobility detector as claimed in claim 11, wherein the controller determines a concentration of the anesthetic agent in the gas sample in response to the ion mobilities of the ions.

13. A modulated aspiration condenser, comprising:
   an ionizer ionizing received gas samples;
   a detection cell receiving the ionized gas samples;
   a reference plate and a collection electrode establishing an electric field in the detection cell to deflect ions contained in the gas sample into the collection electrode, the collection electrode having a characteristic capturing efficiency of the ions; and
   a controller for modulating the capturing efficiency of the collection electrode and detecting an electric current from the collection electrode to determine mobilities and amounts of the ions.

14. A modulated aspiration condenser as claimed in claim 13, further comprising a front electrode positioned upstream of the collection electrode in the detection cell and opposite the reference plate.

15. A modulated aspiration condenser as claimed in claim 13, wherein the controller modulates the capturing efficiency by changing the electric field.

16. A modulated aspiration condenser as claimed in claim 13, wherein the electric field is in a direction transverse to the direction of flow of the gas sample in the detection cell.

17. A modulated aspiration condenser as claimed in claim 13, wherein the gas sample has a concentration of an anesthetic agent which saturates the ionization by the ionizer.

18. An ion mobility detector as claimed in claim 17, wherein the controller determines a concentration of the anesthetic agent in the gas sample in response to the ion mobilities of the ions.

19. A method for detecting ion mobility, comprising:
    ionizing a received gas sample;
    deflecting ions in the ionized gas sample with a time varying electric field;
    detecting degrees of deflection of the ions;
    comparing the detected deflection and corresponding magnitudes of the time varying electric field to identify a type or mobility of the ions.

20. A method as claimed in claim 19, wherein a direction of the electric field is transverse to a direction of flow of the ionized gas sample.

21. A method as claimed in claim 19, wherein the gas sample has a concentration of an anesthetic agent which saturates the ionization in the ionizing step.

22. A method as claimed in claim 21, further comprising determining a concentration of the anesthetic agent in response to the mobility of the ions.

23. A method for detecting molecules in a gas sample, comprising:
    ionizing the gas sample;
    deflecting ions in the ionized gas sample with an electric field established between a reference plate and a collection electrode, the collection electrode having a characteristic capturing efficiency of the ions;
    modulating the capturing efficiency of the collection electrode; and
    analyzing the molecules in response to an electric current of the collection electrode for different capturing efficiencies of the collection electrode.

24. A method as claimed in claim 23, wherein the capturing efficiency is modulated by modulating the electric field.

25. A method as claimed in claim 23, wherein analyzing the molecules includes determining a concentration of the molecules.

26. A method as claimed in claim 23, wherein analyzing the molecules includes determining a type of the molecules.

* * * * *